(12) United States Patent
Bardeau et al.

(10) Patent No.: US 6,551,335 B1
(45) Date of Patent: Apr. 22, 2003

(54) METHODS AND DEVICES FOR STRIPPING BLOOD VESSELS

(75) Inventors: Joël Bardeau, Seilh (FR); Michel Costecalde, Montauban (FR)

(73) Assignee: Astra Tech AB, Molndal (SE)

( * ) Notice: Subject to any disclaimer, the term of this patent is extended or adjusted under 35 U.S.C. 154(b) by 142 days.

(21) Appl. No.: 09/653,018

(22) Filed: Sep. 1, 2000

Related U.S. Application Data

(63) Continuation-in-part of application No. 09/254,498, filed on Dec. 17, 1999, now abandoned.

(30) Foreign Application Priority Data

Jul. 11, 1997 (FR) .............................................. 97 8852
Jul. 8, 1998 (WO) .............................. PCT/FR98/01466

(51) Int. Cl.[7] .............................................. A61B 17/00
(52) U.S. Cl. ....................................................... 606/159
(58) Field of Search ................................ 606/159, 160, 606/108

(56) References Cited

U.S. PATENT DOCUMENTS

| | | | |
|---|---|---|---|
| 2,788,787 A | * | 4/1957 | Trace ........................ 606/159 |
| 2,868,206 A | | 1/1959 | Stoesser ..................... 606/159 |
| 3,788,325 A | | 1/1974 | Jacobsen ..................... 606/159 |
| 6,013,073 A | * | 1/2000 | Choukroun .................... 606/15 |

FOREIGN PATENT DOCUMENTS

| | | | |
|---|---|---|---|
| AU | 60597/69 | | 3/1971 |
| EP | 0477020 A1 | * | 3/1992 |
| FR | 2 619 301 | | 2/1989 |
| FR | 2 727 617 | | 2/1994 |
| WO | WO-9634143 | * | 11/1996 |

* cited by examiner

*Primary Examiner*—Rodney M. Lindsey
*Assistant Examiner*—Shaun R Hurley
(74) *Attorney, Agent, or Firm*—Duane Morris, LLP

(57) ABSTRACT

A blood vessel such as a varicose vein is removed using a semi-rigid rod attached to a flexible thread. The thread is passed through the vein using the rod, which can then be removed. An end of the vein is affixed at a point between the ends of the thread, for example the midpoint. By pulling on the thread, the end of the vein is drawn back into the lumen of the vein, and the vein is progressively turned inside out. A stop can be fixed to the thread slightly beyond the point at which the vein is affixed to the thread, and prevents slipping along the thread. The thread can be at least twice as long as the vein, and alternately pulled in opposite directions.

14 Claims, 3 Drawing Sheets

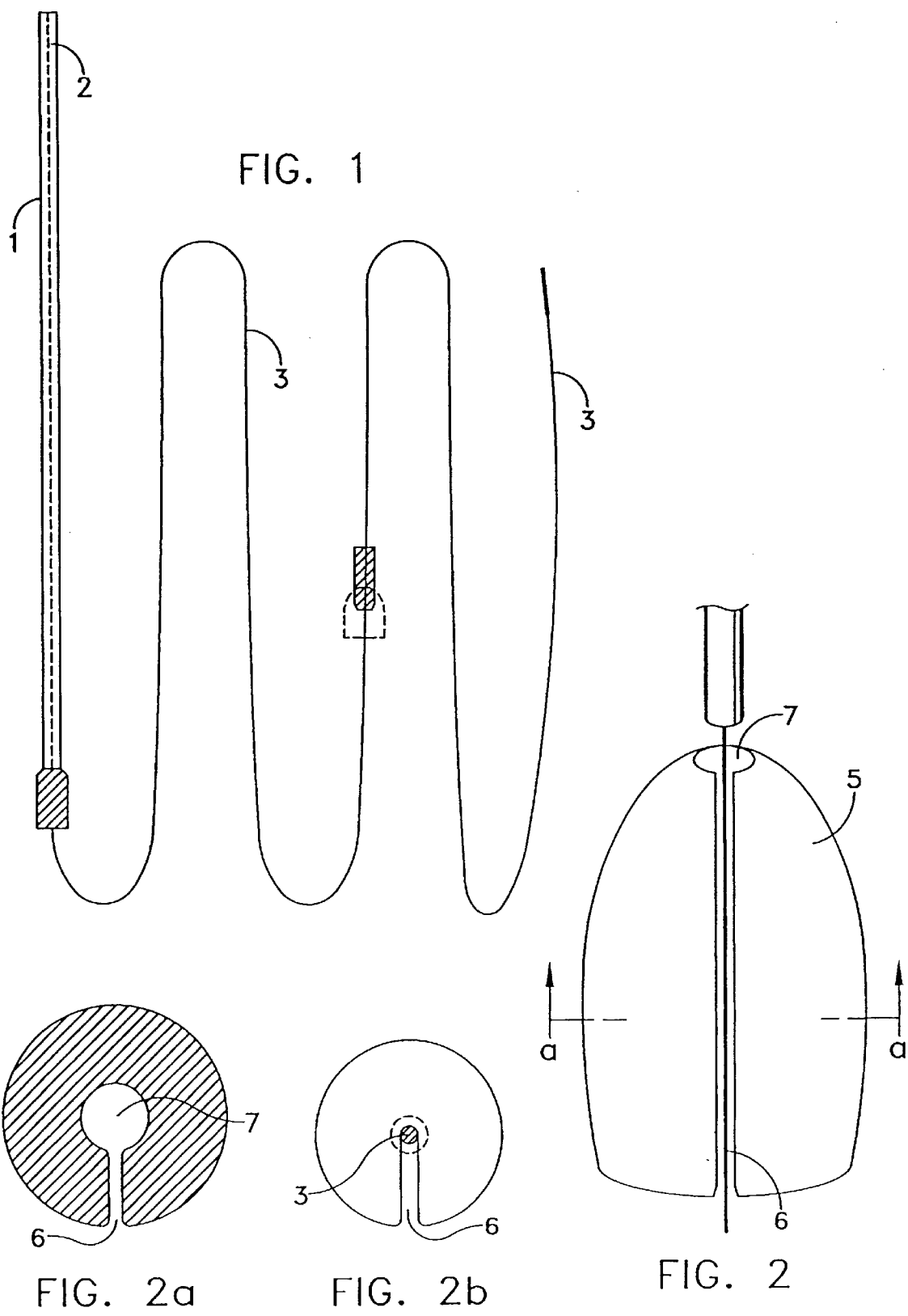

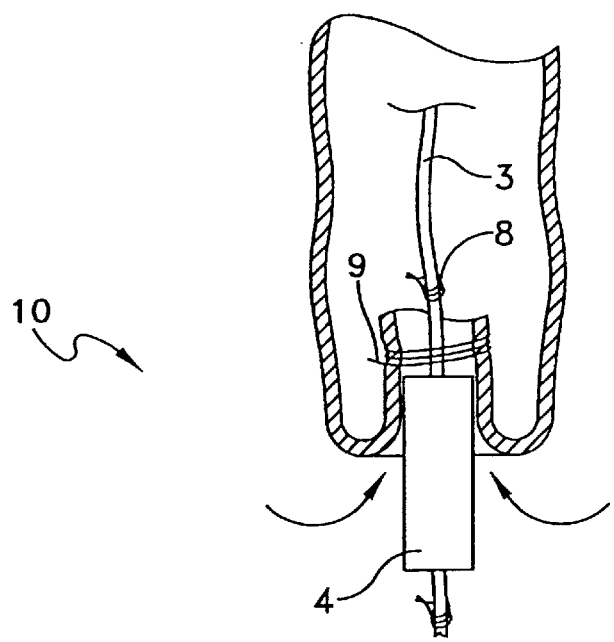
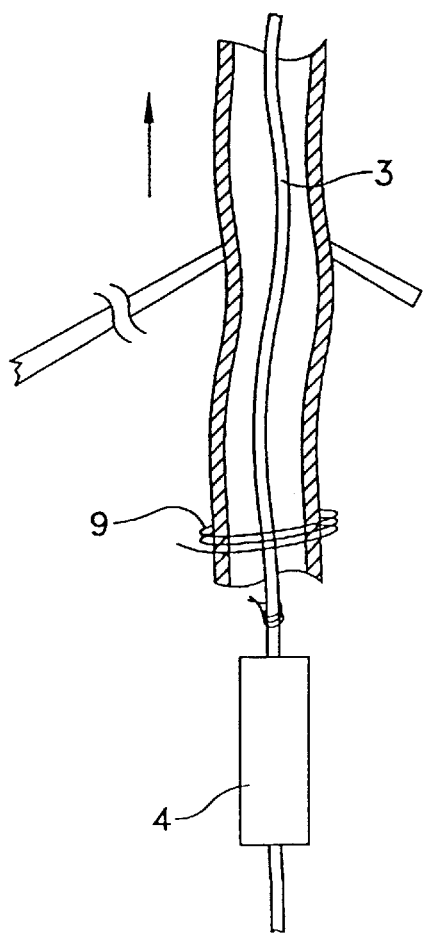
FIG. 3

METHODS AND DEVICES FOR STRIPPING BLOOD VESSELS

CROSS REFERENCE TO RELATED APPLICATION

This application is a continuation-in-part of patent application Ser. No. 09/254,498, filed Dec. 17, 1999 now abandoned.

The present invention relates to surgical methods and devices useful for removal of blood vessels. In particular, the invention relates to surgical methods and devices useful for removal of veins, including varicose veins, from human or animal subjects.

BACKGROUND OF THE INVENTION

Blood vessel removal, and in particular vein removal, is a commonly-used procedure for treatment of conditions such as phlebotomy or saphenectomy. Blood vessel removal procedures generally include stripping out, i.e. removing, a diseased vein, and re-establishment of blood circulation via parallel paths. An entire blood vessel or a segment thereof may be removed.

Common surgical devices useful for removing blood vessels, known as "stripping devices," or "strippers," include a rod, generally a semi-rigid rod, for insertion into the vein that is to be removed. Such devices are rigid or semi-rigid to facilitate catheterization (insertion into) and exeresis (removal) of blood vessels. In common procedures using rigid or semi-rigid rods or similar devices, the rod is inserted into and through the lumen of the vein to be removed. An end of the vein is ligated to the inserted end of the rod. The vein is removed by pulling on the opposite end of the rod to draw the ligated end of the vein or vein segment back toward the rod. The vein is a flexible tube, and pushing against one end of the flexible tube (or, more accurately, pulling backward toward the tube from the ligated end) causes the vein to fold and crumple accordion-wise into a lump of crumpled vein tissue at the end of the rod adjacent to the ligated end. Pulling the rod with this lump at the end, through the patient's tissue for extraction of the vein, may result in injury to adjacent tissue, bleeding, and/or telangiectatic angioma of the skin along the extraction path.

FR-A-2 727 617 describes a vein-removing device for extracting a vein by invagination. The device comprises an elongated rod or wire with an anchoring part formed by a looped-back end of the rod or wire at a distal end, which provides a large diameter structure at the end of the small diameter rod or wire. The rod is inserted in a vein. A ligature is passed around the outside of the vein (and the rod therein) on the proximal side of the large diameter end structure, and cinched to a diameter less than that of the end structure, to fix the vein to the end of the rod. The rod is pulled in the direction of its proximal end, pulling the vein along from the attachment at the distal end of the rod. The rod and the vein can be maneuvered in one direction or in the other direction. In an optional embodiment the rod resides in a plastic sheath that is carried along with the rod. The device still requires a rigid rod even though it could slide in the sheath but for the enlarged structure at the end of the rod, which is wider than the sheath.

AU-B-60597 describes a stripper formed by an oriented monofilament cable whose ends form guides that facilitate snaking of the cable through a vein. A bullet-shaped traveler of a diameter greater than that of the guides is mounted on one of the ends. An end of the vein is attached to the end of the monofilament cable, using a cinched ligature as above. The monofilament cable may not be sufficiently flexible to snake through sinuous paths of some varicose veins, and like other rods that are only somewhat flexible, tends to stretch the vein out straight upon insertion and to crumple the vein along the cable when pulled back.

A need remains for new and/or improved surgical devices for use in partially or completely stripping blood vessels. The present invention is directed to these and other important ends.

SUMMARY OF THE INVENTION

One aspect of the present invention is a device for stripping blood vessels. The device includes a semi-rigid rod having two ends, and a flexible thread secured to one end of the rod for inserting the thread into and through the vein using the rod. The rod can then be removed. The end of the vein is attached at an intermediate point along the thread. The thread is used bidirectionally for pulling the vein generally in one direction for stripping but also permitting reversal of direction to back up and try again in passing sinuous passages and other structures that may impede progress.

Preferably, the length of the thread is at least about twice the length of the rod, so that the rod can be used to insert the thread sufficiently to bring a midpoint of the thread up to an end of the vein. Thus half of the thread extends through the vein to the insertion point and the other half protrudes beyond the vein from the end opposite from the insertion point. This opposite end of the vain is attached to the thread at the midpoint of the thread. Both ends of the thread remain accessible throughout the procedure and permit the midpoint and attached end to be pulled back and forth.

By pulling the thread in one direction, the end of the vein is pulled back by the thread into the lumen of the vein, progressively turning the vein inside out and following along the path of the vein as it is stripped out without forming a lump on the thread. At any snags or obstructions that are encountered, the thread can be pulled from the other end for a short distance (i.e., in the opposite direction) and then reversed again in an effort to pass by the snag or obstruction and continue stripping the vein.

Preferably the vein is stripped entirely in this manner, but it is possible that the vein may crumple and collapse on the thread in the area leading up to the midpoint and the ligated end. Therefore, in some embodiments of the invention, the device further comprises a stop element that can be affixed on the thread. Preferably the stop element is located at about the middle of the thread. The stop element has a larger diameter than the vein and positively crumples the vein on the thread leading to the stop element. The stop element is used if the surgeon gives up the attempt to strip the vein in the preferred way, namely by turning it inside out while pulling the ligated end back into the lumen of the vein.

In preferred embodiments, the thread is made of a polymeric material. The thread can be thin and flexible and of sufficient strength to be pulled manually from either end during the stripping procedure.

Another aspect of the present invention is a method for removing a blood vessel from a part of a body of a patient. The method includes making a first incision and a second incision in the portion of the body from which the blood vessel is to be removed, namely to gain access to a first end of the blood vessel proximate to the first incision and a second end proximate to the second incision. The next step is incising and extracting the first end of the blood vessel; and incising and extracting the second end of the blood vessel. A semi-rigid rod is inserted into the blood vessel from one end (the first end of the blood vessel) and at the insertion end of the rod carries along a flexible thread. The rod and the thread it carries are moved through the blood vessel until substantially all of the rod is inserted and the insertion end carrying the thread emerges from the second end of the blood vessel. The thread is at least twice the length of the blood vessel, and protrudes at both ends of the blood vessel. A midpoint of the thread is located at or near one end of the blood vessel (e.g., the first end), where a length of thread at least as long as the blood vessel extends out of the blood vessel. At the opposite end of the blood vessel (a second end), the thread protrudes at least slightly. The thread can be grasped manually or with a tool at both ends of the blood vessel.

The first end of the blood vessel is affixed to the thread at the midpoint. The first end can be sutured to the thread. The blood vessel is stripped or removed by pulling the thread in a direction from the first end of the blood vessel toward the second end of the blood vessel. The rod, which is needed only to insert the thread initially through the blood vessel so as to be accessible at both ends, can be removed. Both ends of the thread remain accessible until the vein is completely stripped out. At any point in the procedure, a stop can be affixed on the thread near the end of the blood vessel on the first side. The stop has a greater diameter than the blood vessel or the diameter of the blood vessel is cinched ahead of the stop to prevent passage of the stop therethrough, or the blood vessel is ligated to the thread or the stop. When using the stop, the blood vessel may become crumpled along the thread. The stop can be used if necessary to strip the blood vessel, namely when pulling the vein backwards from the midpoint of the thread encounters problems such as an obstruction preventing further progress.

These and other aspects of the invention will be apparent to those skilled in the art in view of the present disclosure and the appended claims.

BRIEF DESCRIPTION OF THE DRAWINGS

Certain features of a preferred embodiment of the present invention are illustrated according to a non-limiting example and with reference to the accompanying figures, in which:

FIG. 1 is a view of a stripper of the invention; and

FIGS. 2, 2a, and 2b are views of the traveler or stop that can be fitted to the thread.

FIG. 3 is a schematic illustration of the use of a preferred device of the invention in removing a vein.

DETAILED DESCRIPTION

Figure 4:
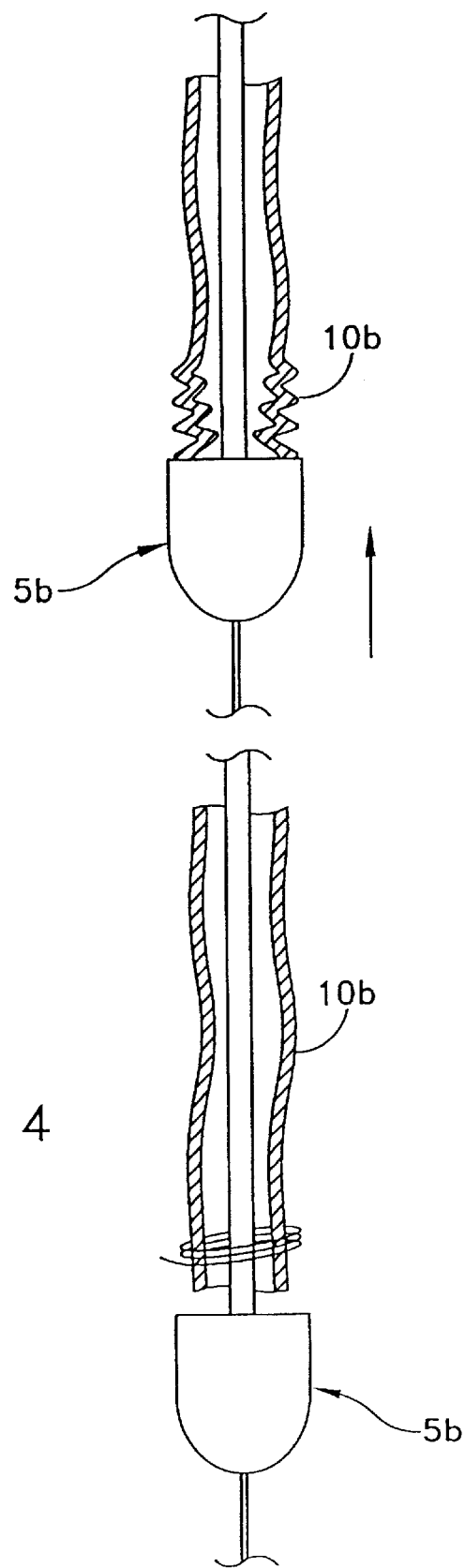
FIG. 4 is a schematic illustration of vein removal by exostripping using a conventional device.

According to the invention, it has been found that trauma to internal structures surrounding a vessel to be stripped is reduced, by using a device which includes a thread for withdrawing a blood vessel. The thread is initially placed by pushing a semi-rigid rod through the blood vessel for guiding the thread into and through the blood vessel. An end of the vessel is affixed to the thread. The thread is preferably long enough to protrude from the blood vessel at both ends throughout the procedure. That is, the thread is at least twice as long as the length of blood vessel to be stripped, and the end of the vessel is affixed to the thread at or near the midpoint of the thread. Thus the thread can be pulled from either opposite end. The thread rather than the rod functions to strip the blood vessel. The rod can be removed before pulling the affixed end of the vessel backwards into the lumen of the vessel to remove the vein by invagination. Alternatively, the rod can be retracted as the thread pulls and strips the vessel. This method reduces trauma as compared to blood vessel removal using conventional devices wherein the blood vessel is pulled out while carried on and affixed to the end of a semi-rigid rod, which typically causes the vessel to crumple and fold into a knot adjacent to the end of the rod.

The methods and devices of the present invention use a thread to remove a blood vessel, rather than a rigid or semi-rigid rod. However, in preferred embodiments, the devices of the present invention include a semi-rigid rod at least for placing the thread and optionally to assist in guiding it. The semi-rigid rod may be made of any biologically compatible material. "Semi-rigid," as used herein to refer to the rod, means having a rigidity sufficient to allow a free end of the rod to be pushed through a blood vessel from the other end, without being hindered in its motion by friction or by contact with the wall of the blood vessel, while having a flexibility sufficient that the rod will travel through moderate curves in the blood vessel in conformity to the structure of the blood vessel, thus eliminating or minimizing the chance of rupture of the blood vessel by the rod. The rod is preferably made of a biologically-compatible material, such as a polymeric material, but can also be flexible metal, e.g., stainless steel. The semi-rigid rod functions substantially as a guide or bodkin for the thread.

The methods and devices of the invention preferably remove a blood vessel such as a vein by endostripping. "Endostripping," as used herein, means extraction of a blood vessel by causing the blood vessel to invaginate from an end attached to the thread and turning the blood vessel "inside out," as shown in FIG. 3. The longitudinal displacement of apparatus or tissues relative to one another, and much of the trauma, occurs inside of the vessel being stripped. In contrast, conventional methods for removing a blood vessel involve "exostripping." "Exostripping" as used herein, means pulling the vessel longitudinally out of the patient's tissues, typically causing the vessel to collapse in an accordion-fold manner, as shown in FIG. 4, and wherein longitudinal relative displacement and resulting trauma occurs between the outside of the vessel and the surrounding tissues. In exostripping as shown in FIG. 4, traveler 5b is located at the end of vein 10b and when pulled upward as shown, causes the vein to crumple.

The rod is preferably made of a biocompatible polymeric, e.g., plastic, material, and may be reinforced by a metal core. Preferably, the rod is substantially cylindrical with a blunt end. The rod has a cross-sectional diameter that is at least about a third of the inside diameter of the blood vessel. Also preferably, the rod has a diameter of not more than about nine tenths of the inside diameter of the vessel. The length of the rod is determined in part by the length of the blood vessel to be removed, and is preferably at least about 2 cm longer than the blood vessel. For example, the rod may be about 1 to 1.5 meters long for removing varicose veins in the legs. Preferably, the thread is at least twice as long as the rod, e.g., about 2 to about 3 meters long, and more preferably, at least 2 cm longer than twice the length of the rod. In some preferred embodiments the rod may be about 1.2 meters long and the thread may be about 2.5–2.6 meters long. In other preferred embodiments, the length of the thread may be substantially greater than that of the rod, such as about 2.2, 2.3 or 2.5 times the length of the rod. While there is no particular upper limit for the ratio of the length of the thread to the length of the rod, if the thread is three times or more of the length of the rod, handling of the device may be cumbersome and the thread may become twisted or tangled. Determination of the appropriate length of the thread and the rod is within the purview of one skilled in the art.

The rod may be substantially straight. Optionally, at its distal end (namely the free end that is inserted into the vessel), the semi-rigid rod may have a pigtail-type coil which in conventional manner, facilitates catheterizing the vein or other vessel by leading the rod along the path of the vein.

The thread may be made of any biologically compatible material having a flexibility sufficient to travel through the blood vessel without causing substantial trauma to the vessel and while substantially conforming to the configuration of the blood vessel. Surgical suturing thread is suitable for use in the devices of the present invention. Exemplary suitable materials for the thread include biologically compatible polymers in one strand or multiple strands. A preferred polymer is a polyamide. Preferably, the thread is sufficiently strong that it will not be broken by tension sufficient to remove a blood vessel. For example, a thread having a breaking strength of at least about 350 kilograms is easily strong enough for use in the methods and devices of the invention.

The thread preferably has a stop element located substantially in the middle thereof. The stop element may be, for example, bullet shaped or cylindrically shaped, or may be substantially ring shaped. The diameter of the stop element is not critical, but preferably the stop element is larger than any opening at the knot, loop or the like by which the end of the blood vessel is attached to the thread. Thus the stop provides a positive point along the thread past which the knot, loop or the like cannot pass. Preferably, the diameter of the stop element is not more than about 1.5 times the diameter of the thread, more preferably not more than about 1.2 times that of the thread. Also preferably, the stop element is crimped or compressed down onto the thread to keep the stop element from moving along the thread. The stop element also can serve as a stopping structure for holding the position of a detachable traveler to be used when the device is used for conventional exostripping rather than endostripping as accomplished according to the invention. Advantageously, the stop element is relatively smooth for sliding past tissues with minimal trauma.

In preferred embodiments, the methods and devices of the invention are used for endostripping as described. However, in some embodiments, the methods and devices of the invention also may be used for exostripping. For example, during an attempt at removal of a blood vessel by endostripping, the blood vessel may become punctured or otherwise damaged to an extent that the rod and the thread penetrate the wall of the blood vessel or otherwise are improperly positioned for invagination or turning the vessel inside out by drawing the end into the lumen of the vessel. In that event, a "traveler" may be applied to the thread so that the blood vessel may be removed by exostripping, i.e. direct removal without invagination by crumpling the vessel along the thread adjacent to the traveler, which can be laterally placed onto the thread adjacent to the stop.

The methods and devices disclosed herein are particularly suitable for removal of veins, e.g., saphenae in various possible modalities, and in particular in the anterograde or retrograde senses. Long or short stripping, and endostripping or exostripping, may be accomplished. If necessary, collateral blood vessels may be progressively sectioned to facilitate removal of a blood vessel using the methods and devices disclosed herein.

In preferred embodiments, vein removal using a device described herein including a semi-rigid rod, a flexible thread and a stop element, is performed as follows, as illustrated in FIG. 3. Two incisions are made at opposite ends of a section of a vein to be removed, detaching and providing access to the vein at the ends of the section. The vein section can also be detached from any small veins and tributary vessels that meet the section laterally. A flexible thread 3 having a knot 8 approximately at a midpoint of thread 3 is inserted into vein 10, using the semi-rigid rod 2 to guide the thread 3 into the vein until the thread passes through the section of vein and emerges at the other end. The rod can then be removed, with the thread protruding from each end of the vein section, and through the incisions. Preferably, the thread protrudes slightly from one end at which the thread will be pulled, namely the proximal end. The thread protrudes to a greater extent at the opposite or distal end, such that the stop element 4, which is near the midpoint of the thread, is located at or near the distal end of the vein section. The thread is secured to the vein, e.g., by a suture 9, placed on the proximal side of the stop element 4, at or near the distal end of the vein section. Traction is applied by pulling on the thread at the proximal end from the point of incision. As the thread is drawn back toward the proximal side, the vein turns inside out, proceeding from the distal end of the vein section toward the proximal end. The attached distal end of the vein section passes into and through the lumen of the vein section to eventually emerge at the proximal end. The application of traction is continued from the proximal end until the entire vein has been turned inside out and extracted through the incision at the proximal side.

In using the methods and devices described herein, it is highly preferred that the vein is not torn or punctured during removal, which keeps the vein intact to be turned back upon itself, inside-out, during stripping. However, if a vein does tear, it is not necessary to repeat from the beginning and catheterize again. Preferably the thread is sufficiently long that, following a tear in a vein, the stop element can be affixed to the vein at the opposite end from where it was initially affixed, and traction applied in the opposite direction to remove the vein. In the event of repeated failures, such as by further tears in the vein, the thread can be used for exostripping, after first passing the traveler 5 laterally onto thread 3 via slot 6, shown in FIGS. 2a, 2b.

The methods and devices described herein can be used, for example, to remove a vein from the leg of a patient. For example, a vein can be removed by providing incisions at the ankle and groin and passing the thread from the ankle incision upward until the thread emerges at the groin. The vein is affixed to the thread just above the stop element, then located at the ankle. The thread is engaged at the groin and pulled upward from the ankle, thereby turning the vein inside out and advancing the ankle end of the vein through the vein and up to the groin, in the anterograde direction. The stop element 4 thus travels along the vein to the groin. Continued pulling on the thread and the vein completes the stripping of the vein, which is removed inside out through the groin incision. Endo-vein removal can also be accomplished downwards in a similar manner. The choice of which direction to proceed in can be made, for example, by preference or to reduce the risk of damage to the adjacent internal saphenous nerve.

In FIG. 1, it can be seen that the stripper comprises a semi-rigid rod 1 having a front portion 2. Optionally, the end of the rod that is introduced into the vein can be straight, or may be rounded, bullet shaped, or coiled to facilitate catheterization of the vein. In a preferred embodiment, as shown, the length of the rod 1 is about 1.2 meters (m) in length so that its front end 2 can travel along the entire length of a vein. In this embodiment, flexible thread 3 is crimped to the rear portion of rod 1. The length of the thread is substantially equal to twice the length of the rod 1, and at least about twice the possible length of a vein to be stripped. At a midpoint of thread 3, a stop element 4 (in the form of a ring, in the depicted embodiment) is crimped down onto thread 3 so as to remain at that position at the midpoint. The stop element 4 functions as an enlargement adjacent to attachment point or ligating point for the vein to the thread, such that the ligation, which may be a loop, is carried along by stop 4 and cannot slide along thread 3.

As mentioned above, the stripper can be used in the anterograde sense or in the retrograde sense, namely in an upward or downward direction considering that the vessel is a vein in a human leg.

FIGS. 2, 2a and 2b show an optional traveler 5, that can be used to form a larger obstruction in the area of stop 4. Traveler 5 can have a lateral or radial slot from the surface to a central axis as shown, whereby traveler 5 can be laterally placed on thread 5 in a manner similar to the attachment of a weight to a fishing line. Traveler 5 is also held against stop 4 and is suitable for use in vein removal by exostripping, namely by crumpling the vein on thread 3 adjacent to traveler 5.

The traveler 5 has a radial slot 6 into which the thread 2 can be inserted as shown in FIG. 2b. At and above level a, shown in FIG. 2, corresponding to the cross-section shown in FIG. 2a, the slot 6 opens out into a radially larger central bore 7. Bore 7 has an inside diameter that is complementary with stop 4. Preferably, bore 7 is slightly smaller than the outside diameter of the stop 4. The traveler can thus be placed laterally on the thread on one side of the stop 4 and forced against stop 4. As stop 4 is forced into bore 7, traveler 5 expands slightly and resiliently at slot 6. This guarantees a secure connection between the traveler and the thread via stop 4.

It will be understood that various changes in the details, materials and arrangements of the parts which have been described and illustrated above in order to explain the nature of this invention may be made by those skilled in the art without departing from the principles and scope of the invention. Although the invention has been described in terms of exemplary embodiments, it is not limited thereto. Rather, the appended claims should be construed broadly, to include other variants and embodiments of the invention which may be made by those skilled in the art without departing from the scope and range of equivalents of the invention.

What is claimed is:

1. A device for removing blood vessels, comprising a semi-rigid rod having a first end and a second end, and a flexible thread attached to the first end of the rod, wherein the thread and the rod are dimensioned such that the first end of the rod can be inserted into and passed through the blood vessel to carry the thread through the vessel for purposes of stripping the blood vessel.

2. The device of claim 1, wherein the length of the thread is at least about twice the length of the rod.

3. The device of claim 1, wherein said thread comprises a biologically compatible polymeric material.

4. The device of claim 3 wherein said biologically compatible polymeric material is a polyamide.

5. The device of claim 1, further comprising a stop element on said thread.

6. A device for removing blood vessels, comprising:

a semi-rigid rod dimensioned to be passed through a section of a blood vessel, the rod having a first end and a second end, and a flexible thread being secured to the first end of the rod, whereby the rod can be inserted in the blood vessel to pass the thread through the vessel for purposes of stripping the blood vessel;

a stop element on said thread; and, wherein said stop element is located at a point spaced from both ends of the thread and provides a stop fixed along thread.

7. The device of claim 6, further comprising a traveler attachable to the thread at the stop element.

8. The device of claim 6, wherein said stop element is located at about a midpoint of the thread.

9. A method for removing from a patient a section of a blood vessel having a predetermined length, the method comprising:

providing a device for removing a blood vessel, said device comprising a semi-rigid rod, a flexible thread longer than the predetermined length, and a stop element fixed along the thread;

selecting a blood vessel and making first and second incisions for access to the section of the blood vessel at a first end and a second end;

inserting said semi-rigid rod into said blood vessel through said first incision and passing the rod through said blood vessel until the thread protrudes from the second incision;

removing said rod, leaving at least a portion of said thread protruding from each of said first incision and said second incision, with said stop element protruding beyond said second incision;

securing said thread to said blood vessel at said stop element;

applying traction to said thread by pulling on said thread at the proximal end from the point of incision, thereby invaginating the vessel from the distal end toward the proximal end; and continuing to apply said traction until said blood vessel is removed.

10. The method of claim 9, wherein the thread is at least twice the predetermined length and further comprising exerting said traction on said thread alternately in opposite directions to assist in passing an obstruction.

11. The method of claim 9, further comprising attaching a traveler to the thread adjacent to the stop element.

12. The method of claim 9, wherein said blood vessel is a vein.

13. The method of claim 12, wherein said vein is a varicose vein.

14. The method of claim 11, wherein said vein is located in a leg of said patient.

* * * * *